United States Patent [19]

Spörk et al.

[11] 4,032,557

[45] June 28, 1977

[54] PROCESS FOR PREPARING ORGANOSILOXANES

[75] Inventors: Helmut Spörk, Altotting; Rudolf Strasser, Burghausen; Rudolf Riedle, Burghausen; Wolfgang Jacques, Burghausen; Johann Waas, Burghausen, all of Germany

[73] Assignee: Wacker-Chemie GmbH, Munich, Germany

[22] Filed: Apr. 26, 1976

[21] Appl. No.: 680,309

[30] Foreign Application Priority Data

May 15, 1975 Germany ............... 2521742

[52] U.S. Cl. ............... 260/448.2 E; 260/46.5 R; 260/448.8 R
[51] Int. Cl.² ............... C07F 7/08; C07F 7/18
[58] Field of Search ............... 260/448.2 E, 448.8 R

[56] References Cited

UNITED STATES PATENTS 3,803,195   4/1974   Nitzsche et al. ............ 260/448.2 E Primary Examiner—Paul F. Shaver

[57] ABSTRACT

An improved process for preparing organosiloxanes and alkyl halides by passing organohalosilanes and alkanols having 1 and/or 2 carbon atoms through at least one layer of packing material which is maintained at a temperature of from 60° to 150° C, the improvement which comprises (1) recycling from 1 to 6 liters of an aqueous phase separated from the organosiloxanes emerging from the layer or layers of packing material for each mol of organohalosilane introduced into the layer or layers of packing material and (2) reacting the organosiloxane separated from the aqueous phase with from 2 to 10 percent by weight based on the weight of the organosiloxane with the same organohalosilane which is passed through the layer or layers of packing material.

6 Claims, 1 Drawing Figure

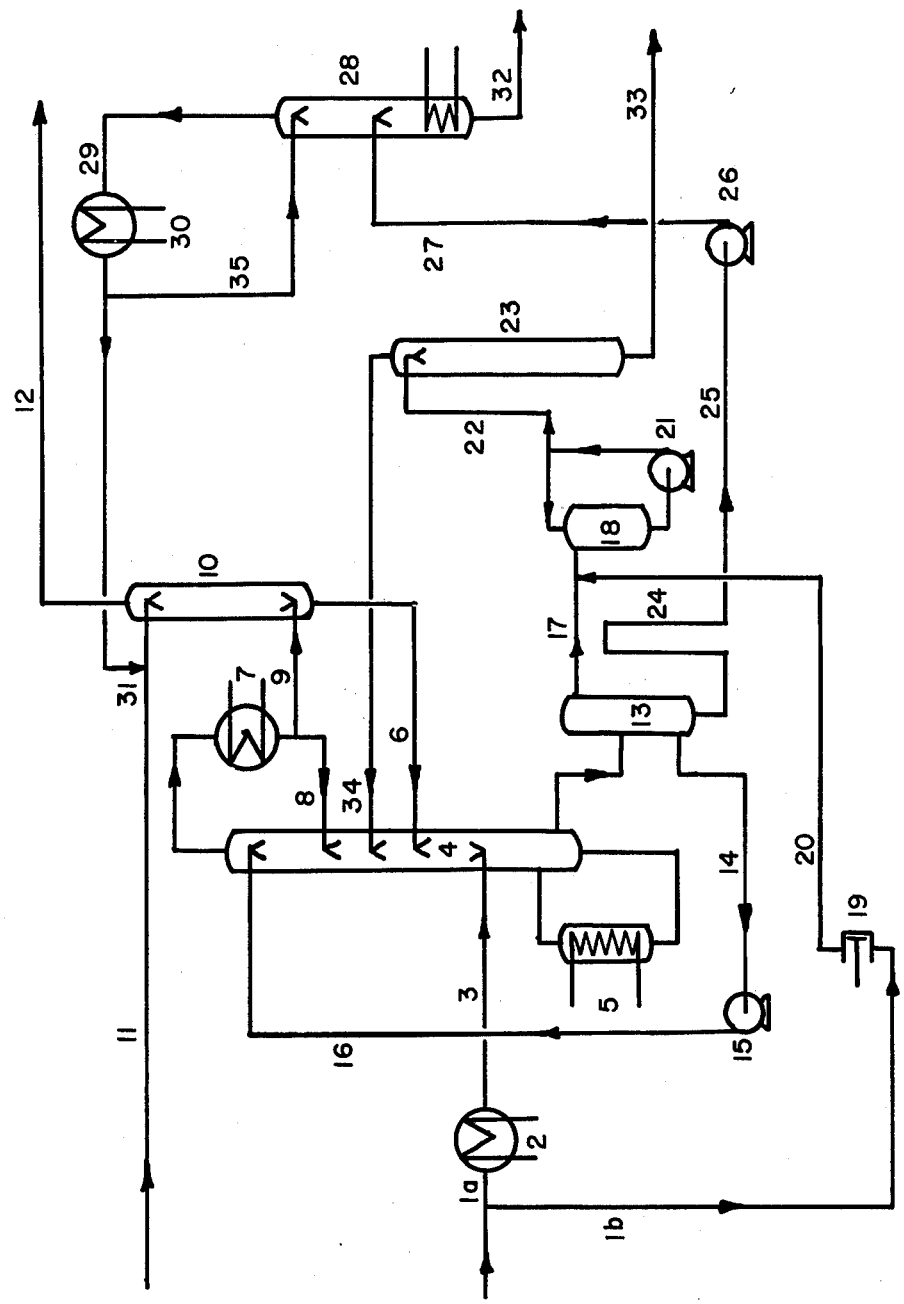

PROCESS FOR PREPARING ORGANOSILOXANES

This invention relates to a process for preparing organosiloxanes and alkyl halides and more particularily to an improved process for preparing organosiloxanes and alkyl halides by passing organohalosilanes and alkanols having one and/or two carbon atoms through at least one layer of packing material.

Heretofore, organosiloxanes and alkyl halides have been prepared by passing organohalosilanes and alkanols having one and/or two carbon atoms through at least one layer of packing material maintained at a temperature in the range of from 60° to 150° C. (See German patent application No. 2,148,699). According to the process described in the German patent application, the excess alcohol recovered from the layer or layers of packing material is distilled to reduce its water content below 10 percent by weight before it is recycled to the layer or layers of packing material.

Compared to the process described in German patent application 2,148,669, the process of this invention offers several advantages. For example, it permits a greater space-time yield economy. Also, the organopolysiloxanes are substantially free of Si-linked alkoxy groups and the alkyl halides contain a lower percentage of dialkyl ethers. Furthermore, a substantial savings is realized in having to distil only a portion of the total amount of the excess alcohol emerging from the layer or layers of packing material prior to recycling the alcohol to said layer or layers of packing material.

Therefore, it is an object of this invention to provide a process for preparing organosiloxanes and alkyl halides. Another object of this invention is to provide a process for preparing organosiloxanes which are substantially free of alkoxy groups. A still further object of this invention is to provide a process for preparing alkyl halides containing a smaller percentage of dialkyl ethers. A further object of this invention is to provide a process for preparing organosiloxanes and alkyl halides in which only a portion of the excess alcohol recovered from the layer or layers of packing material is distilled before being recycled to the layer or layers of packing material.

The foregoing objects and others which will become apparent from the following description are accomplished, generally speaking, by providing a process for preparing organosiloxanes and alkyl halides by passing organohalosilanes and alkanols having one and/or two carbon atoms through at least one layer of packing material which is maintained at a temperature of from 60° to 150° C., the improvement which comprises (1) recycling to the layer or layers of packing material, from 1 to 6 liters of the aqueous phase which separates from the organosiloxanes emerging from the layer or layers of packing material for each mol of organohalosilane conveyed to the packing material and (2) reacting the organosiloxane which separates from the aqueous phase with from 2 to 10 percent by weight based on the weight of the organosiloxane of the identical organohalosilane that is introduced into the layer or layers of packing material.

The organohalosilanes used in the process of this invention may be the same organohalosilanes as have been used heretofore in preparing organosiloxanes and alkyl halides by passing organohalosilanes and alcohols, esters or ethers through at least one layer of packing material.

Organosilicon compounds which contain at least 90 percent by weight of halosilanes are employed in the process of this invention, in which the silicon valences of said organosilicon compounds are saturated with at least 1 or 2 halogen atoms and at least one SiC-linked organic radical, preferably having from 1 to 6 carbon atoms. Examples of organosilicon compounds in which the silicon valences are saturated with 1 or 2 halogen atoms and at least one SiC-linked organic radical, preferably having from 1 to 6 carbon atoms, are organosilanes corresponding to the formula $R_mH_nSiX_{4-m-n}$, as well as organosilanes of the formula $XSi(R_2)R'Si(R_2)X$. In the above formulas, X represents chlorine, bromine or iodine and because of its availability, chlorine is preferred; R represents a monovalent, or substituted monovalent hydrocarbon radical, preferably having from 1 to 6 carbon atoms; R' represents a divalent hydrocarbon radical and a substituted divalent hydrocarbon radical, preferably having from 1 to 6 carbon atoms; $m$ is 1, 2 or 3, preferably 2; $n$ is 0 or 1 and the sum of $m + n$ is 2 or 3.

Examples of monovalent hydrocarbon radicals represented by R are alkyl radicals, such as methyl, ethyl and propyl radicals; cycloalkyl radicals, such as the cyclopentyl and the cyclohexyl radicals; alkenyl radicals, such as the vinyl radical; cycloalkenyl radicals such as the cyclohexyl radical and aryl radicals, such as the phenyl radical.

Examples of suitable divalent hydrocarbon radicals represented by R' are methylene, ethylene and phenylene radicals.

The substituted hydrocarbon radicals represented by R and R' are those which preferably do not cause excessive cross-linking under the selected reaction conditions. Examples of preferred hydrocarbon radicals represented by R' are haloalkyl radicals in which the halogen atom or atoms are linked in an alpha and/or gamma position to the silicon atoms, such as in the case of the 3-chloropropyl radical and the 3,3,3-trifluoropropyl radical, as well as haloaryl radicals, such as o-, p-, and m-chlorophenyl radicals.

Generally, the dimethylsiloxane units are the predominate organosiloxane units of the organopolysiloxane products produced, in accordance with this invention. These include the organopolysiloxane elastomers and diorganopolysiloxanes which are endblocked with trimethylsiloxy groups and which are liquid at room temperature. Since chlorine is readily available, dimethyldichlorosilane is the preferred organohalosilane to be used in the process of this invention. Nevertheless, other organosilicon compounds may be used instead of or together with the dimethyldichlorosilane, provided that the silicon valences are saturated with 1 or 2 halogen atoms and has at least one Si-linked organic radical. Examples of other organohalosilanes which may be employed are vinylmethyldichlorosilane, phenylmethyldichlorosilane, divinyldichlorosilane, diphenyldichlorosilane, methyldichlorosilane, ethyldichlorosilane, diethyldichlorosilane, trimethylchlorosilane and vinyldimethylchlorosilane.

Thus it is possible to use in the process of this invention dimethyldichlorosilane, mixtures of dimethyldichlorosilane and at least one additional organohalosilane as well as mixtures of organohalosilanes.

In addition to the organosilicon compounds in which the silicon valances are substituted by 1 or 2 halogen atoms and have at least one SiC-linked organic radical, other halosilanes may be present in an amount of up to 10 percent based on the total weight of the silanes employed. Examples of these halosilanes are silicon tetrachloride and methyl trichlorosilane. Silanes which have more than 2 halogen atoms per molecule are generally present as impurities. It is essential that not more than 10 percent by weight of the silanes have more than 2 halogen atoms per molecule, otherwise a considerable degree of cross linking will occur which will plug the equipment.

Alkanols which have 1 or 2 carbon atoms can be either methanol or ethanol or mixtures of methanol and ethanol. Methanol is of course readily available. Likewise, methyl chloride is particularly desirable as an alkyl halide because methyl chloride can, for example, be used in the synthesis of dimethyldichlorosilane. Thus methanol is the preferred alkanol to be employed in the process of this invention.

However, it is not essential to the process of this invention that an alkanol be used as such. It is possible to produce the alkanol in-situ by the hydrolysis of carboxylic acid esters having from 2 to 4 carbon atoms. The hydrolysis can be achieved by means of the hydrogen halide, especially hydrochloric acid, evolved from the process of this invention. Thus, this process provides a means for utilizing a mixture containing equal mol parts of methanol and methyl acetate. This mixture is obtained as a by-product, for example, in the manufacturing of polyvinyl alcohol through the transesterification of polyvinyl acetate.

Generally from 1 to 1.75 mols and more preferably 1 mol of alkanol having 1 and/or 2 carbon atoms per gram-atom of halogen on the silane is added to the reaction vessel. It is preferred that there always be an excess of alkanol in the layer or layers of packing material when the organohalosilanes are passed therethrough.

The packing material must be substantially inert under the reaction conditions and must be impervious to acids. Examples of suitable packing materials are those which are ceramic- or carbon-based, such as Berl-saddles, Rasching rings and rings having protrusions which are made of pressed ceramic and graphite materials, such as graphite rings. Additional examples of packing materials which may be employed in the process of this invention are fritted polyolefin powders and/or other acid-resistant synthetic resins as well as silicon dioxide xerogels (see H. Rompp "Chemie-Lexikon," 6th Edition, Stuttgart 1966, column 5915, 16).

Also compounds which promote the reaction between the alkanols and the organohalosilanes in the production of organosiloxanes and alkyl halides may be used. Suitable examples of other compounds which may be employed are zinc chloride, or sulfuric acid. Moreover, it is possible to use compounds as packing material which promote the reaction, such as cation exchangers with an H-shape. However the use of such compounds which promote the reaction is not preferred, since these promoting compounds may result in the dissociation of the SiC-bonds.

Mixtures consisting of various packing materials can be used as well. It is preferred that the amount of packing material be at least 50 percent by volume based on the total volume of the reactants and reaction products which come in contact with the packing. The length of the packing layer or layers is preferably at least 30 cm for each liter based on the total amount of organohalosilanes and alkanols which pass through the packing. There is no upper limit as to the length of packing layer or layers.

It is preferred that the packing layer or layers be maintained at a temperature in the range of from 70° to 120° C. At temperatures below 60° C the conversion of organohalosilanes and akanols into organosiloxanes and alkyl halides requires a longer reaction time than is generally desirable. When the temperature of the packing exceeds about 150° C, the quality of the organosiloxanes may deteriorate, due to the dissociation of SiC-bonds.

The aqueous phase which separates from the organosiloxanes ermerging from the packing, generally consists of at least 70 percent by weight of water and hydrogen haldie, e.g., hydrogen chloride, with the amount of hydrogen chloride generally being on the order of from 21 to 26 percent by weight based on the total weight of water and hydrogen chloride. The balance of the aqueous phase consists essentially of methanol and/or ethanol and possibly some carboxylic acid having from 1 to 3 carbon atoms. It is surprising that the formation of alkyl halide in almost quantitative yield is achieved by the process of this invention, since from 1 to 6 liters of the aqueous phase which separates from the organosiloxanes emerging from the layer or layers of packing are recycled for each mol of organohalosilanes introduced into the packing material. Moreover, since a substantial amount of water is present during the reaction of the alkanols with the organohalosilanes and during the production of methyl chloride from methanol and hydrogen chloride at temperatures below 200° C, a dehydration agent such as tin chloride is generally employed. (See for example L. Gatterman "Die Praxis des organischen Chemikers," Berlin 1947, pages 91/92).

In a preferred embodiment of this invention, from 1 to 6 liters of the aqueous phase separated from the organosiloxanes emerging from the layer or layers of packing material are recycled directly to the packing layer for each mol of the organohalosilanes without first separating any of the components, such as for example, the alkanol from the aqueous phase.

Since 1 to 6 liters of the aqueous phase separated from the organosiloxanes emerging from the layer or layers of packing material are recylced for each mol of the organohalosilanes introduced into the layer or layers of packing material in accordance with this invention, the addition of from 1 to 1.75 mols of alkanol for each gram-atoms of halogen on the silane contained in the packing material in the reaction vessel results in an alkanol concentration in the packing material of from 7 to 50 percent by weight, preferably from 20 to 30 percent by weight based on the total weight of alkanol, water and hydrogen halide.

The layer or layers of packing material are preferably placed in a pipe-shaped reaction vessel in a vertical position, i.e., a reaction tower. However, the latter's position may be in a horizonal or in a diagonal position as well. If a reaction tower is used as the reaction vessel, the alkanol is preferably placed in the reaction tower above the opening through which the organohalosilanes are introduced and the organosiloxanes are withdrawn from the bottom of the tower or at least from the lower one third of the tower. It is preferred that the opening through which the organohalosilanes are introduced be at a distance of at least 20 cm from the opening through which the alkanol is introduced.

The process of this invention is preferably carried out at atmospheric pressure, i. e. at 760 mm Hg (abs) or at approximately 760 mm Hg (abs); however, it may be carried out at subatmospheric or superatmospheric pressures. It is preferred that the pressures and temperatures be selected so that the water which is present in the packing layer or layers and the water conveyed to the packing layer be in a liquid state.

The reaction between the organohalosilanes and alkanols can be conducted either in a parallel or a counter-current flow apparatus; however, it is preferred that these reactants flow in a counter-current manner in the reaction apparatus.

The reaction between the organosiloxanes which are separated from the aqueous phase and from 2 to 10 percent by weight based on the weight of the organosiloxanes of the same type of organohalosilanes as conveyed to the packing, occurs during the mixing of the organosiloxanes and the organohalosilanes. Generally, the reaction occurs within from 1 to 20 minutes due to the elevated temperature of the organosiloxanes. When these organosiloxanes emerge from the packing material which is maintained at a temperature between 60° and 150° C and are separated from the aqueous phase, they are generally in a temperature range of from 40° to 80° C.

The process of this invention is preferably carried out as a continuous process. Even though corrosion and possibly temperature resistant material is used for all components of the processing apparatus which come in contact with hydrogen chloride, the equipment employed requires only a very small investment, since large quantities can be processed in small volume equipment.

Excess alkanol which may be present in the aqueous phase separated from the organosiloxanes emerging from the packing material and which is not recirculated to the layer or layers of packing material, can be recycled into the reaction vessel upon removal of the water.

As long as the reactants, such as the organohalosilanes remain liquid or gaseous at the temperature which prevails in the packing material, the process of this invention does not require the presence of other materials such as organic solvents.

In addition to the organosiloxanes and alkyl halides, the process of this invention produces small amounts of aqueous hydrogen chloride, especially hydrochloric acid, dimethyl ether, diethyl ether, or methylethyl ether, which occur as by-products in smaller amounts then have been formed heretofore in the known processes.

The yield of organosiloxanes is practically quantitative and the yield of alkyl halides exceeds about 93 percent of theoretical.

Organosiloxanes which are produced in accordance with this invention can be either linear or cyclic. Where the production of exclusively linear organosiloxanes is desired, then the cyclic organosiloxanes which are separated from the mixture of organosiloxanes emerging with the aqueous phase from the packing material are recycled through the packing material. When only cyclic organosiloxanes are to be produced, then linear organosiloxanes which are separated from the mixture of organosiloxanes emerging with the aqueous phase from the packing material are again recycled through the packing material.

In the preferred embodiment, at least one layer of packing material is maintained at a temperature of about 100° C at approximately 760 mm Hg (abs), and if dimethyldichlorosilane is used as the organohalosilane and if an excess of alkanol, e.g., methanol, is in contact with the packing material, then linear dimethylpolysiloxanes having a viscosity of from 70 to 200 cSt at 25° C are obtained along with cyclic dimethylpolysiloxanes, hydrogen chloride and methylchloride. The viscosity of the dimethylpolysiloxanes is thus sufficiently low to allow it to be pumped without difficulty, while on the other hand its viscosity is sufficiently high to permit the dimethylpolysiloxanes to be used directly with condensation catalysts such as phosphonitrile chlorides for the production of high-molecular weight dimethylpolysiloxanes which may be used in the production of elastomers.

In addition to the hydrogen halide which is added to the layer or layers of packing material in the recycled aqueous phase, additional gaseous or alkanol dissolved hydrogen halides of the same type as those which are present in the recycled aqueous phase may be introduced into the packing material. This embodiment results in the production of additional alkyl halides and thus permits the use of hydrogen halides which could not be used otherwise.

A preferred embodiment of the invention is illustrated in the flow diagram.

Liquid dimethyldichlorosilane is transferred through conduit 1 to evaporator 2. The evaporated dimethyldichlorosilane is then passed into reaction tower 4 via conduit 3. The reaction tower 4 is filled with packing material (not shown in the diagram) and is heated with the aid of a forced circulation evaporator 5.

Liquid methanol enters the reaction tower 4 via conduit 6. Unreacted methanol in the vapor phase and methyl chloride formed in the reaction tower 4 are collected in condenser 7. Condensed methanol is recycled to the reaction tower via conduit 8. Uncondensed methanol and methyl chloride are transferred through conduit 9 to a scrubber 10, where the methyl chloride is scrubbed with fresh methanol from conduit 11. The scrubbed methyl chloride passes from the scrubber 10 via conduit 12 to a condensation apparatus (not shown in the diagram).

The product emerging from the bottom of the reaction tower 4 is separated in separator 13 into an upper phase which consists primarily of dimethylpolysiloxane and a lower aqueous phase which consists substantially of water, hydrogen chloride and methanol.

A protion of the lower phase formed in separator 13 is transferred to the distillation apparatus 28 via an adjustable interface level regulator 24, conduit 25, pump 26 and conduit 27. The distillation residue obtained in the distillation apparatus 28 consists essentially of about 20 percent by weight of aqueous hydrochloric acid and is removed through conduit 32. The methanol exiting from the top of the distillation apparatus 28 is transferred to condenser 30 via conduit 29. A portion of the methanol which is condensed in condenser 30 is recycled via conduit 35 to the distillation apparatus 28. The balance of the condensed methanol from condenser 30 is passed through conduit 31 where it is mixed with fresh methanol via conduit 11 before it enters scrubber 10 from where it goes back to the reaction tower 4 via conduit 6. The balance of the lower phase formed in separator 13 is recycled via conduit 14 and pump 15 through conduit 16 to the layer or layers of packing material in the upper third of the reaction tower.

The upper phase which formed in separator 13 is transferred to mixing vessel 18 via conduit 17 together with the dimethyldichlorosilane which is passed through conduit 1b via dosing pump 19 and conduit 20. The reaction product containing dimethylpolysiloxane which is mixed with dimethyldichlorosilane is pumped by pump 21 via conduit 22 into the distillation apparatus 23, where extractive distillation is carried out with the aid of aqueous steam at a temperature of about 112° C to separate the low-boiling dimethylpolysiloxanes containing mostly cyclic dimethylpolysiloxanes, hydrogen chloride, (about 30 grams per liter of dimethylpolysiloxane via conduit 22), methyl chloride and methanol from the non-volatile linear dimethylpolysiloxanes.

The non-volatile linear dimethylpolysiloxanes are removed from the distillation apparatus 23 through conduit 33. After the dimethylpolysiloxanes have been separated from the aqueous phase in a separator (not shown in the diagram), they are recylced to the reaction tower 4 via conduit 34.

In the following examples all percentages are by weight unless otherwise specified. The figures in the parenthesis refer to the reference numbers illustrated in the flow diagram.

EXAMPLE

The reaction tower 4 contains 12 vertical superposed glass tubes which are held by flanges and 400 mm long connectors with an inside diameter of 300 mm. The glass tubes are 1000 mm long, their inside diameter is 300 mm and they are filled with 1.5 inch wide ceramic rings which have hook-shaped protrusions which rest on perforated carbon plates. This packing material is commercially available under the name "Novalox." The tower's total height is 14,500 mm.

Reaction tower 4 is supplied with liquid methanol via conduit 6 at a point which is about 6,000 mm from the bottom of tower 4. Liquid methanol is passed through conduit 6 until a constant stream of methanol circulates through conduits 14 and 16 as well as the separation apparatus 13.

Thereafter liquid dimethyldichlorosilane is introduced into the evaporator 2 via conduits 1 and 1a. The evaporated dimethyldichlorosilane is introduced into the lower section of the reaction tower 4 via conduit 3 which opens into the reaction tower at a point which is about 1500 mm from the bottom of tower 4. As soon as the dimethyldichlorosilane reaches the reaction tower 4 the methanol supply through conduit 6 is regulated so that it provides 1 mol of methanol for each mol of dimethyldichlorosilane coming through conduit 3 and the tower's contents are heated to 100° C by means of the steam heated glass forced circulation evaporator 5. As soon as a temperature of 100° C is reached, the methanol supply entering via conduit 6 is increased to 2 mols of methanol for each mol of dimethyldichlorosilane from conduit 3.

Thirty minutes after the dimethyldichlorosilane has been added, unreacted methanol and methyl chloride pass in the vapor phase from the top of the reaction tower 4 into condenser 7. Condensed methanol returns to the reaction tower via conduit 8. Uncondensed methanol as well as methyl chloride is transferred through conduit 9 to scrubber 10 where the methyl chloride is washed in a counter-current stream. The scrubber 10 consists of a vertical 2000 mm high pipe with an inside diameter of 150 mm. The pipe is filled with the same packing material as the reaction tower 4 and equipped with a reflux cooler which operates with water at a temperature of about 12° C. Conduit 9 opens into the lower section of the scrubber 10, e.g., about 400 mm above its bottom. The methyl chloride which has been washed with methanol from conduits 11 and 31 is removed from the scrubber 10 via conduit 12 and conveyed to a condensation device (not shown in the diagram).

The product is removed at the bottom of the reaction tower 4 and is transferred to separator 13 where it enters at a location that is about 600 mm above the bottom of the separator. The separator 13 consists of a vertical 900 mm long pipe which has an inside diameter of 300 mm. In separator 13 the product received from the bottom of reaction tower 4 is separated into an upper phase which consists essentially of dimethylpolysiloxanes and a lower phase which constitutes the aqueous phase.

About 1000 liters per hour of the lower phase which forms in separator 13 are recirculated via conduit 14, centrifugal pump 15 and conduit 16 to the layer of packing material which is about 500 mm below the upper end of reaction tower 4, where methanol is present in the packing material in a concentration of about 25 percent based on the total weight of water, methanol and hydrogen chloride. The remainder of the lower phase formed in separator 13 is transferred to distillation apparatus 28 via controlled interface regulator 24, conduit 25, pump 26, and conduit 27 where it enters at a point about 1200 mm above the bottom of apparatus 28. The distillation apparatus 28 consists of 5 superposed vertical 1000 mm long glass tubes which are connected by flanges. The glass tubes are filled with ½ inch wide Intalox saddles (see "Ullmanns Encyklopadie der technischen Chemie," 4th Edition, volume 2, Weinheim 1972, page 529). The total height of the distillation device 28 is 5300 mm. The methanol vapor which exits from the top of distillation apparatus 28 is conveyed to condenser 30 via conduit 29. About 80 percent by weight of the methanol which is condensed in condenser 30 returns to the distillation apparatus 28 via conduit 35. About 20 percent by weight of the methanol condensed in condenser 30 reaches conduit 31. The methanol distillation thus provides for a recycling ratio of about 1:4. The distillation residue is removed from the bottom of distillation apparatus 28 through conduit 32. The methanol transferred through conduit 31 mixes with fresh methanol from conduit 11 and is conveyed to scrubber 10 from which it returns to reaction tower 4 via conduit 6.

The upper phase formed in separator 13 is transferred to an 18-liter capacity mixing vessel 18 through conduit 17 which exits about 850 mm above the bottom of separator 13, together with the dimethyldichlorosilane which is conveyed through conduit 1b, via dosing pump 19 and through conduit 20 at a ratio of 3.9 percent based on the weight of the dimethylpolysiloxanes conveyed through conduit 17. The reaction product which has been obtained in the previously described manner as well as through the recirculation of dimethylpolysiloxanes mixed with diemthyldichlorosilane via the centrifugal pump 21, is conveyed to the distillation apparatus 23 via conduit 22. In the distillation apparatus 23, extractive distillation is performed with aqueous steam at a temperature of 112° C (whose introduction into the distillation apparatus 23 is not shown in the flow diagram), and the dimethylpolysiloxanes, hydrogen chloride, methyl chloride and methanol distillable under these conditions are separated from non-volatile linear dimethylpolysiloxanes. The desired non-volatile linear dimethylpolysiloxanes are drawn from the distillation apparatus 23 through conduit 33. The cyclic dimethylpolysiloxanes are separated from the aqueous phase in a separator (not shown in the flow diagram) and then recycled via conduit 34 to reaction tower 4 at a point which is about 7000 mm above the bottom of the reaction tower.

After constant reaction conditions are achieved, conduits 1, 1a and 1b supply a total of 31.0 liters of dimethyldichlorosilane per hour. Conduit 1a supplies 29.3 liters of dimethyldichlorosilane per hour to evaporator 2 and ultimately to reaction tower 4, while conduit 1b supplies 1.7 liters of dimethyldichlorosilane per hour via pump 19 through conduit 20. Conduit 6 conveys about 20 liters of methanol per hour to reaction tower 4. The scrubber 10 is supplied with 9.2 liters of fresh methanol per hour via conduit 11 and with 0.8 liter of recovered methanol via conduit 31. About 27.72 kg of cyclic organopolysiloxanes are recycled through conduit 34 to reaction tower 4. Conduit 33 supplies 18.78 kg per hour of dimethypolysiloxanes having an Si-linked hydroxyl group in each of its terminal units and has a viscosity of 120 cSt at 25° C. These dimethylpolysiloxanes contain less than 1 mg of hydrogen chloride and a maximum of one Si-linked methoxy group for each 350 Si-linked hydroxyl groups and after 2 hours of heating at 250° C exhibits a decrease in weight of about 0.25 percent. Conduit 12 supplies 10.9 m³ of methyl chloride per hour which contains less than 1 mg of hydrogen chloride per kg and only 1.7 percent of dimethyl ether.

| RESULTS OF 744 HOURS OF OPERATION | | | |
|---|---|---|---|
| Reaction Components | Liters | kg | kmol |
| Dimethyldichlorosilane (gaseous) | 23064 | 24447 | 189.5 |
| Methanol (liquid) | 14285 | 11428 | 357.1 |
| Mol ratio (CH₃)₂SiCl₂ : CH₃OH = 1 : 1.88 | | | |
| Reaction Products | Liters | kg | kmol |
| Dihydroxydimethyl-polysiloxane | 13972 | 13749 | 185.8 (calculated as) (CH₃)₂SiO) |
| Yield: 98% of theory | | | |
| Methyl chloride per 1000 liters (gaseous) | 8109 | 17840 | 353.3 |
| Yield: 93.2% of theory | | | |

COMPARISON EXAMPLE

For purposes of comparison with German Patent Application No. 2,148,669 the process described in the previous Example is repeated, except that conduits 1b, 14, 16 and 20 as well as pumps 15 and 19 are not utilized in this example. Moreover, the aqueous phase which is separated from the organosiloxanes emerging from the layer of packing material is not recycled to the latter and the organosiloxanes which have been separated from the aqueous phase are not recycled with the organohalosilane. Also the temperature of the layers of packing material is maintained in the range of from 65° to 68° C rather than at 100° C. Since the organosiloxanes which have been separated from the aqueous phase are not being recycled to the layers of packing material, higher temperatures cannot be maintained without the use of pressure and equipment which is suited for pressurized operations. Only 10 liters of dimethyldichlorosilane and 7.2 liters of methanol can be reacted per hour.

Conduit 33 yields only 6 kg per hour of dimethylpolysiloxanes having an Si-linked hydroxyl group in each of its terminal units and which has a viscosity of 50 to 60 cSt at 25° C, and at lesat two Si-linked methoxy groups for each 100 Si-linked hydroxyl groups, while the hourly yield of conduit 12 is only 3.3 m³ of methyl chloride which contains from 3 to 4 percent dimethyl ether.

What is claimed is:
1. An improved process for preparing organosiloxanes and alkyl halides by introducing an organohalosilane and alkanol having from 1 to 2 carbon atoms into a reactor containing at least one layer of packing material which is maintained at a temperature of from 60° to 150° C to form an aqueous phase containing organosiloxanes, and thereafter separating the organosiloxanes from the aqueous phase, the improvement which comprises (1) recycling into the reactor from 1 to 6 liters of the aqueous phase for each mol of the organohalosilane introduced into the reactor and (2) reacting the organosiloxanes separated from the aqueous phase with from 2 to 10 percent by weight based on the weight of the organosiloxanes with the same organohalosilane used in the initial reaction.

2. The process of claim 1 wherein from 1 to 1.75 mols of alkanol for each gram-atom of halogen is added to the reactor in addition to the alkanol present in the recycled aqueous phase.

3. The process of claim 2 wherein the reactor contains from 7 to 50 percent by weight of alkanol based on the total weight of alkanol, water and hydrogen halide.

4. The process of claim 1 wherein the alkanol is generated in in-situ by the hydrolysis of carboxylic acid esters having from 2 to 4 carbon atoms.

5. The process of claim 1 wherein the organohalosilane is represented by the formula

in which R is selected from the group consisting of monovalent hydrocarbon radicals and substituted monovalent hydrocarbon radicals having from 1 to 6 carbon atoms, X is a halogen, m is a number of from 1 to 3, n is 0 to 1 and the sum of m + n is 2 or 3.

6. The process of claim 1 wherein the organosilane is represented by the formula

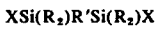

in which R is selected from the group consisting of monovalent hydrocarbon radicals and substituted monovalent hydrocarbon radicals having from 1 to 6 carbon atoms, R' is selected from the group consisting of divalent hydrocarbon radicals and substituted divalent hydrocarbon radicals having from 1 to 6 carbon atoms, X is a halogen, m is a number of from 1 to 3, n is 0 to 1 and the sum of m + n is 2 or 3.

* * * * *